United States Patent
Asmussen et al.

(10) Patent No.: US 6,627,631 B1
(45) Date of Patent: Sep. 30, 2003

(54) PHARMACEUTICAL COMPOSITION CONTAINING DESOXYPEGANINE FOR THE TREATMENT OF ALCOHOLISM

(75) Inventors: Bodo Asmussen, Bendorf (DE); Thomas Hille, Neuwied (DE); Hans-Rainer Hoffmann, Neuwied (DE); Klaus Opitz, Münster (DE)

(73) Assignees: LTS Lohmann Therapie-Systeme AG, Andernach (DE); He Arzneimittelforschung GmbH, Werne (DE)

( * ) Notice: Subject to any disclaimer, the term of this patent is extended or adjusted under 35 U.S.C. 154(b) by 0 days.

(21) Appl. No.: 09/890,085

(22) PCT Filed: Feb. 8, 2000

(86) PCT No.: PCT/EP00/00973
§ 371 (c)(1),
(2), (4) Date: Jul. 25, 2001

(87) PCT Pub. No.: WO00/48600
PCT Pub. Date: Aug. 24, 2000

(30) Foreign Application Priority Data

Feb. 19, 1999 (DE) .......................... 199 06 974

(51) Int. Cl.⁷ .................... A61K 31/495; A61K 31/437; A61K 31/40; A61L 15/42; A61L 15/44
(52) U.S. Cl. .................. 514/250; 514/349; 514/408; 514/631; 514/810; 514/811; 424/444; 424/484; 424/447; 424/449; 604/890.1
(58) Field of Search .................. 514/250, 408, 514/349, 631, 811, 810; 424/444, 447, 449, 484; 604/890.1

(56) References Cited

U.S. PATENT DOCUMENTS

| | | | | |
|---|---|---|---|---|
| 3,742,951 A | * | 7/1973 | Zaffaroni | |
| 3,760,805 A | * | 9/1973 | Higuchi | |
| 3,760,806 A | * | 9/1973 | Leeper | |
| 3,760,984 A | * | 9/1973 | Theeuwes | |
| 3,797,494 A | * | 3/1974 | Zaffaroni | |
| 3,845,770 A | * | 11/1974 | Theeuwes et al. | |
| 3,916,899 A | * | 11/1975 | Theeuwes et al. | |
| 3,987,790 A | * | 10/1976 | Eckenhoff et al. | |
| 3,996,934 A | * | 12/1976 | Zaffaroni | |
| 4,031,894 A | * | 6/1977 | Urquhart et al. | |
| 4,137,300 A | * | 1/1979 | Sheth et al. | |

FOREIGN PATENT DOCUMENTS

DE 33 15272 A1 * 10/1984
FR 2668062 * 4/1992

OTHER PUBLICATIONS

Database WPI Section Ch, Week 197913 Derwent Publications Ltd., London, GB; AN 1979–25213B (XP002139611).*

Dababase WPI Sechtion Ch, Week 198235 Derwent publications Ltd., London, GB, AN 1982–74317E (XP002139612).*

Chemical abstract 105: 17866w.*

* cited by examiner

Primary Examiner—Frederick Krass
Assistant Examiner—Clinton Ostrup
(74) Attorney, Agent, or Firm—Frommer Lawrence & Haug LLP

(57) ABSTRACT

Desoxypeganine and its pharmaceutically acceptable acid addition salts can be used in the treatment of alcoholism. Said substances are administered preferably in a continuos and controlled manner. The pharmaceutical administration form enables controlled release, e.g. for oral, transdermal or another route of parenteral administration.

8 Claims, No Drawings

PHARMACEUTICAL COMPOSITION CONTAINING DESOXYPEGANINE FOR THE TREATMENT OF ALCOHOLISM

DESCRIPTION

Deoxypeganine and its pharmaceutically acceptable acid addition salts can be used for the treatment of alcoholism. These substances are preferably administered in a continuous and controlled manner. The pharmaceutical administration form makes controlled release possible for, for example, oral, transdermal or alternatively parenteral administration.

The invention relates to the use of deoxypeganine and its pharmaceutically suitable acid addition salts for the treatment of alcoholism. These compounds are released in a continuous and controlled manner from appropriate pharmaceutical formulations, which are administered, for example, orally, transdermally or otherwise parenterally.

In particular, the present invention makes pharmaceutical formulations available which release suitable compounds for the treatment of alcoholism in a controlled manner.

While acute withdrawal in alcohol-dependent patients and the treatment of life-endangering withdrawal delirium in special wards is no longer a medical problem today, there is still no satisfactory treatment of chronic alcoholism. About 80% of the treated alcoholics relapse within a year. They need help by means of a reliably acting and highly tolerable agent against the desire for alcohol which leads to the relapse.

In spite of the human problems and of the immense national economic damage associated with the problem of chronic alcoholism, innovation in the medicinal treatment of chronic alcoholism is stagnating worldwide and very particularly in the Federal Republic of Germany.

In the case of the pharmaceuticals which are employed for the control of the effects of alcohol and of alcoholism, the following must be differentiated:

1. Sobering-up agents (amethysts).
2. Agents for the treatment of life-threatening alcohol intoxication, e.g. naloxone (Narcanti), physostigmine.
3. Pharmaceuticals for making acute alcohol withdrawal easier, e.g. neuroleptics (Neurocil, Melleril), piracetam, clonidine, carbamazepine, and withdrawal delirium: clomethiazole (Distraneurin).
4. Substances which block the degradation of alcohol at the acetaldehyde stage and as a result produce an artificial alcohol intolerance. Disulfiram (Antabuse), the main representative of this group, is the medicament which is employed most frequently for the treatment of alcoholism. Antabuse, however, is not a therapeutic, as this and related substances decrease neither the desire for alcohol nor influence the causes of the condition.
5. Agents which are intended to satisfy the compulsive desire for alcohol (the craving) and thus to prevent the relapse of the treated alcoholics. There is an urgent need, in particular, for these agents, but an efficacious medicament for the treatment of chronic alcoholism has still not been found.

Clinical trials with fenfluoramine and bromocriptine have not been repeated and confirmed.

The great hopes which had been placed in the lithium therapy of chronic alcoholism have not been fulfilled.

The best results yet have been achieved with zimelidine, but this serotonin reuptake inhibitor, which was marketed as an antidepressant under the name Normud, had to be withdrawn because of serious side effects and is no longer available. Galanthamine, an alkaloid from Amaryllidaceae, is still being clinically tested at present.

The object of the invention is therefore the provision of a pharmaceutical which, by controlled release of an oral, transdermal or otherwise parenteral formulation, makes an efficacious and practical treatment of alcoholism possible by decreasing the desire for alcohol.

This object is achieved according to the invention by a formulation and its use for the treatment of alcoholism, which formulation comprises an efficacious amount of the active compound deoxypeganine (1,2,3,9-tetrahydropyrrolo[2,1-b]quinazoline) and/or one of its pharmaceutically tolerable acid addition salts.

This achievement is all the more surprising as the pharmacological actions of deoxypeganine have in fact been intensively investigated in the former USSR, but the action of a deoxypeganine-containing formulation, attributed to deoxypeganine, of decreasing the desire of alcoholics for alcohol has not been described up to now.

Deoxypeganine is obtained by isolation from the harmel peganum (Peganum harmala) or by synthesis.

On account of its pharmacological properties, deoxypeganine belongs to the group of reversibly acting cholinesterase inhibitors. It is closely related in its actions to physostigmine, neostigmine and galanthamine, but also has specific properties. Deoxypeganine inhibits not only the degradation of acetylcholine, but also that of dopamine.

This advantage offsets its somewhat lower dose-related cholinesterase inhibitory action. Deoxypeganine was intended in the former Soviet Union as an antidote and prophylactic in poisoning by organic thiophosphoric acid esters.

In contrast to neostigmine, deoxypeganine crosses the blood-brain barrier and antagonizes the cerebral action of cholinergic toxins.

The present invention is directed at formulations by means of which deoxypeganine or one of its pharmaceutically acceptable acid addition salts are released in a continuous, controlled manner.

Pharmaceutical forms which release active compounds in a controlled manner are known in the prior art. The administration of pharmaceutically active compounds by means of such formulations can be carried out orally, transdermally or otherwise parenterally.

The formulations for oral administration suitable in the context of the present invention are described below.

In such a formulation, the pharmaceutical active compound is encapsulated in a semipermeable membrane, e.g. of cellulose acetate. A tiny hole is drilled in the capsule material using a drill or a laser. Water is absorbed by the capsule material in the body of the patient who is being treated. The pharmaceutical active compound is gradually driven through the small opening by osmotic pressure in the desired, constant and controlled manner. Such systems are described in U.S. Pat. Nos. 3,760,805, 3,760,806, 3,764,984, 3,845,770, 3,916,899 and 3,987,790. In these systems, the pharmaceutical active compounds can be present in solid form or absorbed on ion exchanger resins.

Another system for oral administration according to the present invention is described by Sheth and Leeson in U.S. Pat. No. 4,137,300. This patent describes a formulation which comprises a wax matrix.

The active compounds of the present invention are administered in a fitting and suitable manner by means of appropriate formulations. The solid active compounds can be administered in solution or as a dispersion. The solution or dispersion medium can be inorganic or organic. Suitable solution or suspension media for deoxypeganine are, for example, water, silicone oil or mineral oil.

Silicone oils are understood here as meaning linear-polymeric dimethylsiloxanes and mineral oils are understood as meaning the distillation products obtained from mineral raw materials (petroleum, lignite tar and coal tar, wood, peat), which essentially consist of mixtures of saturated hydrocarbons.

In order to make the administration of a compound by means of a formulation as described above possible, the following additives can be added to the system:

antioxidants, synergists, stabilizers, preservatives, flavor corrigents, colorants, solvents, solubilizers, surfactants (emulsifiers, solubilizers, wetting agents, antifoams), viscosity- and consistency-influencing agents, gel-forming agents, absorption accelerators, adsorption agents, moisture retention agents, lubricants (e.g. flow-regulating agents), disintegration- and solution-influencing agents, fillers (extenders), peptizing agents, release-delaying agents.

This list makes no claim to completeness. Many substances fulfil not only one function, they are therefore to be assigned to a number of the excipient groups mentioned. Thus, for example, types of starch are used as fillers in tablet and powder production. However, at the same time they are flow-regulating agents, adsorption agents, hydrogel-forming agents and viscosity enhancers.

The suitable, physiologically acceptable substances are known to the person skilled in the art.

In a formulation for the transdermal administration of compounds according to the present invention, the pharmaceutical active compound can be contained in a matrix from which it is released in the desired gradual, constant and controlled manner. The permeability of the matrix during the release of the compound is based on diffusion. A system of this type is described in German Patent DE 33 15 272. This system consists of an impermeable back layer, a specially constructed supersaturated active-compound reservoir associated with it, made of a polymer matrix, a contact-adhesive layer permeable to the active compound, associated with the reservoir, and a protective layer which can be removed again for use, covering the contact-adhesive layer. Systems in which the reservoir layer has such a high intrinsic tackiness that it is simultaneously the contact-adhesive layer are also possible.

If the active compound is absorbed through the skin, the patient to be treated in this way receives a controlled and predeterminable supply of the active compound.

Other suitable transdermal formulations are described in U.S. Pat. Nos. 3,742,951, 3,797,494, 3,996,934 and 4,031,894. These formulations fundamentally consist of a back layer, which is one of the surfaces, an adhesive layer permeable to the active compound, which is the other surface, and finally a reservoir which comprises the active compound between the two layers forming the surfaces. Alternatively to this, the active compound can also be contained in a multiplicity of microcapsules which are distributed within the permeable adhesive layer. In each case, the active compound is continuously released from the reservoir or the microcapsules through a membrane into the adhesive layer permeable to the active compound, which is in contact with the skin or mucosa of the patient to be treated. In the case of microcapsules, the capsule material can also act as a membrane.

Formulations which are suitable for the otherwise, parenteral administration of deoxypeganine and its salts are those which permit a depot action of the active compound. In this context, the formulation is administered as an injection solution on a nonaqueous basis. The possible solvents are known to the person skilled in the art. Examples which may be mentioned are the vegetable oils which individual pharmacopeias prescribe. Peanut oil, olive oil, almond oil, sunflower oil, soybean oil and sesame oil are prominent. Castor oil often shows a particularly favorable solubility for medicaments; in addition oils of animal origin are also suitable. The oils are physiologically indifferent and highly tolerable. The prerequisite for this is that they are specially purified and have low acid and peroxide counts. As intravenous administration is not possible because of the lack of miscibility with the blood serum and can lead to pulmonary embolism, only their use for intramuscular and subcutaneous injection preparations is possible. Oily solutions and suspensions remain at the site of administration for a very long time (often up to 1 month) and release the active compounds over a prolonged period.

The dose of deoxypeganine or its pharmaceutically acceptable acid addition salts must be so high that a lasting action is achieved and needs individual adjustment. The active compound content of the present formulation is preferably between 0.1 and 90% by weight, in particular preferably between 5 and 20% by weight, based on the total weight of the formulation.

The invention is illustrated by the following example:

EXAMPLE

Influence of deoxypeganine HCl on the voluntary alcohol consumption of genetic ethanol-preferring rats.

The experimental animals were in each case 6 female rats of a strain which goes back to the Finnish AA rat line. The animals of this inbred strain prefer 10% alcohol as a drinking liquid if pure water is additionally offered to them (free choice).

The animals were kept individually in type 3 Makrolon cages at a room temperature of 23° C. and air changes nine times per hour. Dry feed granules (Altromin 1311; meal to which vitamins, minerals, amino acids and trace elements are added; manufacturer: Altromin Spezialfutterwerke GmbH, Lage), drinking water and ethanol solution (10% v/v) were available to them in unrestricted amounts only during the dark phase from 20.00 hours to 08.00 hours, namely in special vessels which guarantee loss-free feeding and drinking. The amounts consumed were determined gravimetrically; the amounts of drink automatically and continuously with the aid of twelve weighing cells. The respective proportion of ethanol solution to the total amount of drink in % served as a measure of the alcohol preference: 0% means that only water, no ethanol solution, was drunk, 100% means that exclusively ethanol solution was drunk. The average alcohol preference of the untreated experimental animals was 78% or 83%.

The results are reproduced in the following table:

Table: Influence of deoxypeganine HCl on the ingestive behavior of female ethanol-prefering rats (n=6). The values determined during the three-day preliminary period in each case are in round brackets.

| Dose [mg/kg orally] | 15 | 30 |
|---|---|---|
| Body weight, BW [g] | 215 ± 6.2 | 213 ± 4.9 |
| Alcohol preference [%] | (82.8 ± 6.4) | (77.8 ± 4.3) |
|  | 45.0 ± 12.9** | 51.7 ± 6.4*** |
| Alcohol consumption, absolute [g/kg of BW] | (6.47 ± 0.43) | (6.30 ± 0.34) |
|  | 3.17 ± 0.89** | 3.71 ± 0.42*** |
| Total amount of drink [g/kg of BW] | (97.2 ± 2.3) | (100.9 ± 1.9) |
|  | 89.8 ± 5.6 ns | 90.6 ± 6.1 ns |
| Food intake [g/kg of BW] | (55.2 ± 1.3) | (55.7 ± 2.1) |
|  | 57.7 ± 2.6 ns | 44.6 ± 7.6 ns |

Student's t-test for paired values
**p <0.01
***p <0.001
ns = not significant

As the table shows, the desire for alcohol can be considerably reduced by administration of deoxypeganine. Food intake and total amount of drink are not significantly changed.

What is claimed is:

1. A method for treating alcoholism which comprises administering an effective amount of a pharmaceutical formulation comprising deoxypeganine and/or its pharmaceutically acceptable salts to a patient in need thereof.

2. The method according to claim 1, wherein the pharmaceutical formulation is administered transdermally, orally or parentally.

3. The method according to claim 1, wherein the pharmaceutical formulation contains from 0.1 to 90% by weight of deoxypeganine and/or one of its pharmaceutically acceptable salts based upon to total weight of the pharmaceutical formulation.

4. The method according to claim 2, wherein the pharmaceutical formulation contains from 5 to 20% by weight of deoxypeganine and/or of its salts, based upon total weight of the pharmaceutical formulation.

5. The method according to claim 1, wherein the pharmaceutical formulation has a depot action.

6. The method according to claim 1, wherein the pharmaceutical formulation is a solution or is a dispersion wherein deoxypeganine and/or one of its pharmaceutical salts is dispersed in an organic or an inorganic medium.

7. The method according to claim 1, wherein the pharmaceutical formulation is a transdermal therapeutic system, said system comprising an impermeable back layer, an active compound reservoir, which contains deoxypeganine and/or its pharmaceutically acceptable salts, optionally a contact adhesive device, for fixing the transdermal system to the skin, and optically a removable protective layer.

8. The method according to claim 7, wherein the transdermal therapeutic system administers the deoxypeganine and/or its pharmaceutically acceptable salts to the patient in a controlled and continuous manner.

* * * * *